(12) United States Patent
Kuo et al.

(10) Patent No.: US 8,583,399 B2
(45) Date of Patent: Nov. 12, 2013

(54) METHODS FOR BEHAVIOR PATTERN ANALYSIS

(75) Inventors: Bo-Jau Kuo, Taipei (TW); Ching-Hsiu Yang, Taipei (TW)

(73) Assignee: National Yang Ming University, Taipei (TW)

( * ) Notice: Subject to any disclaimer, the term of this patent is extended or adjusted under 35 U.S.C. 154(b) by 538 days.

(21) Appl. No.: 12/905,782

(22) Filed: Oct. 15, 2010

(65) Prior Publication Data

US 2012/0029865 A1 Feb. 2, 2012

(30) Foreign Application Priority Data

Jul. 27, 2010 (TW) .............................. 99124781 A

(51) Int. Cl.
*G06F 15/00* (2006.01)

(52) U.S. Cl.
USPC ........ 702/141; 702/19; 702/188; 340/539.12; 340/573.1; 600/300

(58) Field of Classification Search
USPC ............ 702/19, 141, 188; 340/539.12, 573.1; 600/300
See application file for complete search history.

(56) References Cited

U.S. PATENT DOCUMENTS

| 6,605,038 B1* | 8/2003 | Teller et al. ................... 600/300 |
| 2002/0084902 A1* | 7/2002 | Zadrozny et al. .......... 340/573.1 |

\* cited by examiner

*Primary Examiner* — Jonathan C Teixeira Moffat
*Assistant Examiner* — Hien Vo
(74) *Attorney, Agent, or Firm* — Muncy, Geissler, Olds & Lowe, PLLC

(57) ABSTRACT

A method for behavior pattern analysis is provided in which the behavior signals of a subject are continuously detected using tri-axis accelerator. The behavior signals are divided as a plurality of time windows based on a predetermined time length. The plurality of time windows are configured as an X-Y matrix, and cross analysis is performed on the time windows as X-axis and Y-axis to obtain a plurality of correlation coefficients as being the preferred correlation values. A pattern with bright spots and dark spots is plotted according to the preferred correlation values, and behavior pattern is evaluated from the number and distribution of bright spots and the pattern. The behavior consistency of a subject can be efficiently evaluated, and his/her behavior abnormality, disease development or other situations can be determined accordingly.

4 Claims, 5 Drawing Sheets

METHODS FOR BEHAVIOR PATTERN ANALYSIS

BACKGROUND OF THE INVENTION

1. Field of the Invention

The present invention relates to a method for behavior pattern analysis, particularly to a method for behavior pattern analysis by using tri-axis acceleration signal detection technology.

2. Prior Art

Detection and analysis for a body's behaviors have been applied in various fields. For instance, an athlete's repeated activities are detected, and the similarity among his activities and the correct activity is analyzed so that the athlete learns the activities faster and more precise. In addition, the repeated activities of a human or an animal are detected, and behavior abnormality or disease development of the human or the animal is analyzed according to the number and frequency of the repeated activities. Alternatively, a human's abnormal activities or activity sequence is detected to alarm at the early stage whether the slip risk would be happened, so that detection can be applied in medical healthcare industry.

At present, the detection method for physical activity is performed using the current accelerator to detect the number of human's acceleration behind a predetermined threshold. For instance, when a subject's acceleration is behind 0.025 g, the value behind this threshold is recorded as one activity, and the number of activities within a time unit is the determined value. The drawback of this method lies in that the activities with lower acceleration and higher counts would be enlarged and the activities with higher acceleration and fewer counts would be narrowed to result in overestimate or underestimate for the activity calculation. Therefore, it is important to efficiently and precisely detect and analyze the human activities with different degree on determining human behavior and physical/psychological situations.

Taiwan Patent No. I296786 discloses a portable movement monitor system and a method thereof, wherein the movement monitor data of a subject is collected using a portable data collect unit which wirelessly transmits the movement monitor data to a distributed data server. Nevertheless, the postures and posture variations of the subject only can be determined on home care, but behavior abnormality or disease development of the subject cannot be evaluated during the test.

Taiwan Patent Publication No. 200842653 discloses an analytic method for human activity distribution, in which the acceleration signals produced upon the subject moves are detected, and the acceleration displacement track data of the subject is calculated, and the acceleration displacement track data is analyzed using human activity distribution analysis device. However, the application is suitable for the video games analyzed on human activities and postures, but it does not teach to analyze and generalize on activity signals. Equally, the application cannot be used on evaluating behavior abnormality and disease development of a subject.

It is therefore attempted by the applicant to deal with the above situation encountered in the prior art.

SUMMARY OF THE INVENTION

In the present invention, a tri-axis acceleration sensor or a device having a tri-axis accelerator is used to detect the variations of acceleration motion of a subject within the test time. The variations of acceleration are divided as n time windows according to the time interval, and n is an plural number. The n time windows are configured as an X-Y matrix, cross analysis is performed on n time windows at X-axis and n time windows at Y-axis, and the largest correlation coefficient is the preferred correlation value for this analysis. Thus, a plurality of preferred correlation values ($n^2$) are obtained. The plurality of preferred correlation values then are converted as bright spot signals and dark spot signals, and a pattern is formed by combining bright spot signals and dark spot signals. The behavior consistency of a subject is evaluated according to the distribution of bright spot signals in the pattern and the pattern diagram, and his/her behavior abnormality, disease development or other situations can be determined accordingly.

DETAILED DESCRIPTION OF THE INVENTION

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

In the prevent invention, the tri-axis acceleration sensor is disposed on the accessories such as clothes, pants, shoes, necklace, belt and so on, or is attached on the head, hand, leg, body and so on, and electrocardiogram and tri-axis acceleration signals are detected using current technologies. Alternatively, the tri-axis acceleration sensor can be incorporated with other devices, such as an micro type wireless apparatus for collecting electrocardiogram signals (referring to Taiwan Patent No. I313593). Since the tri-axis acceleration sensor records three channels, the acceleration component values at X, Y and Z axes respectively (the acceleration at each time point), a total amount A (unit: gravity (g)) at each time point for three points in three channels is calculated using Equation I:

$$A=\sqrt{(X^2+Y^2+Z^2)} \qquad \text{Equation I,}$$

where value A is the power combining three components at x, y and z axes, and value A is verified with values at x, y and z axes. The verified amplitude values at each time interval (e.g. about one second) are calculated using RMS (root mean square) Equation II, and the verified amplitude values are the acceleration variance amount to react human behavior. Therefore, the variance of human movement can be recorded using RMS Equation:

$$RMS = \sqrt{\frac{\sum_{t=1}^{n}(Amp(t))^2}{n}},\quad \text{Equation II}$$

where n is the total amount of data points sampled during a specified time segment, t is the individual time point (1 to n) with an increment of 1/sampling rate, and Amp(t) is the amplitude of the data point at a given time point.

Figure 1:
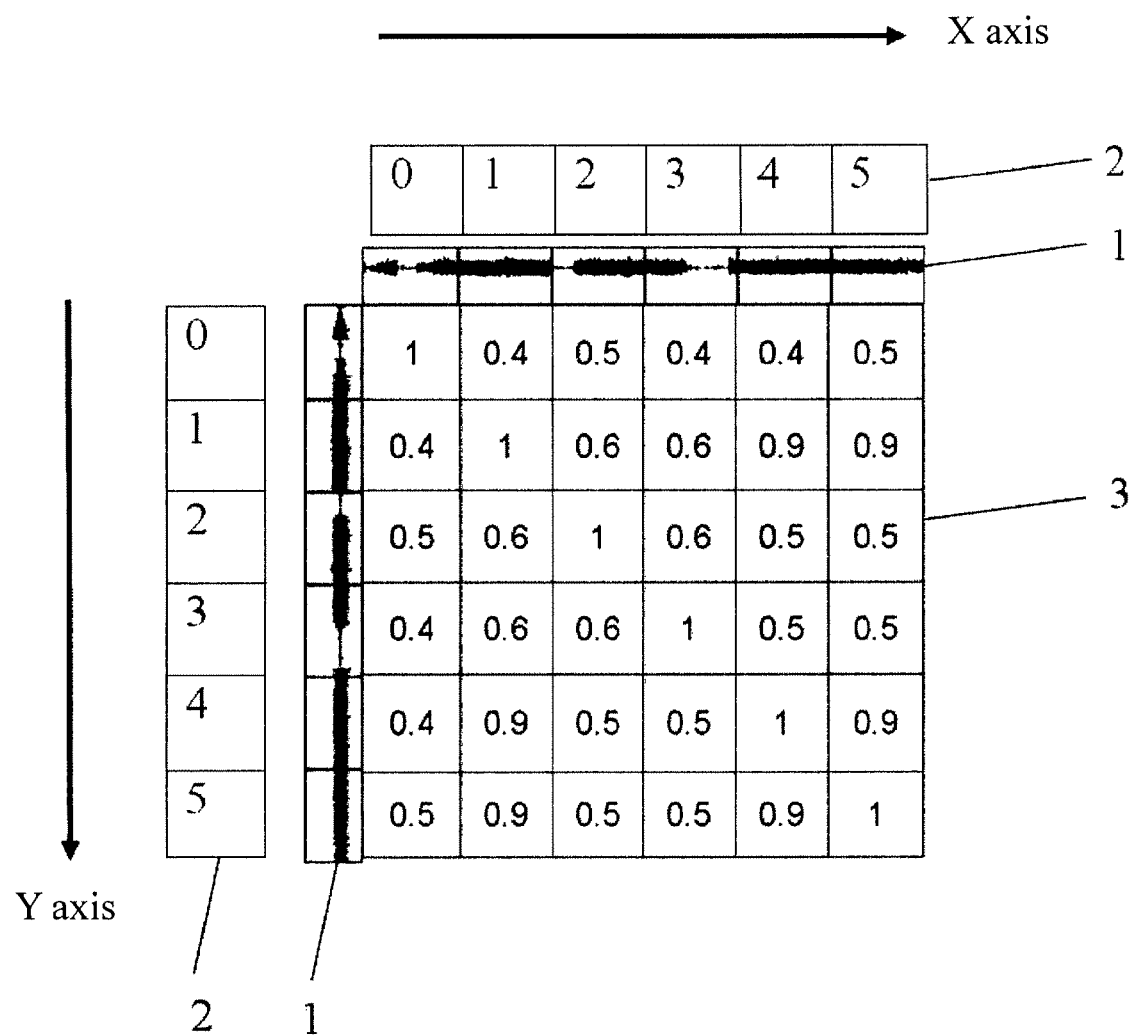
FIG. 1 is a matrix diagram showing the method for behavior pattern analysis in the present invention.

Please refer to FIG. 1, which is a matrix diagram showing the method for behavior pattern analysis in the present invention. After human movements are successively detected using tri-axis acceleration sensor, the successive detection signals 1 are divided as a plurality of time windows 2(n), including the zeroth time window, the first time window, ... and the (n−1)th time window. In the first preferred embodiment of FIG. 1, the time windows 2 is divided as a total of 6 time windows. The divided time windows 2 is configured at X axis and Y axis respectively, wherein the zeroth time window at X axis (abbreviated as time window $X_0$) is neighbored to the zeroth time window at Y axis (abbreviated as time window $Y_0$), and the (n−1)th time window at X axis (abbreviated as time window $X_{n-1}$) and the (n−1)th time window at Y axis (abbreviated as time window $Y_{n-1}$) respectively are situated at the end of X axis and that of Y axis. The cross analysis is pairwisely performed on X-axis time windows and Y-axis time windows. For example, time window $X_0$ and time window $Y_1$ are analyzed, and time window $X_2$ and time window $Y_3$ are analyzed. In the matrix of FIG. 1, there are a total of 36 analytic results. Upon cross analysis, the largest correlation coefficient or coherence is adapted to be the preferred correlation value for the analysis, and thus one cross analysis for each pair has a preferred correlation value. The cross analysis further includes cross-correlation analysis and cross-spectral analysis.

Next, these preferred correlation values are converted as the brightness of spots. Each cross analysis for time windows are sequentially shown as the values at X and Y axes, and thus each cross analysis result is plotted as a spot. These spots are plotted on a screen or a surface to obtain a specific pattern, and the bright spots are referred to that two behaviors at different time points have high consistency. Oppositely, the dark spots are referred to that two behaviors at different time points lack correlation. In addition, if dark spots are predominantly shown on the pattern, it indicates that human movements are not consistent from beginning to end; and if bright spots occupies most area of the pattern, it indicates that human movements have high consistency.

FIG. 2 to FIG. 5 shows the results for behavior pattern analysis on the subject according to the aforementioned method. Analytic time is 10 minutes, and time length of the time window is 2 seconds with a total of 300 time windows.

Figure 2:
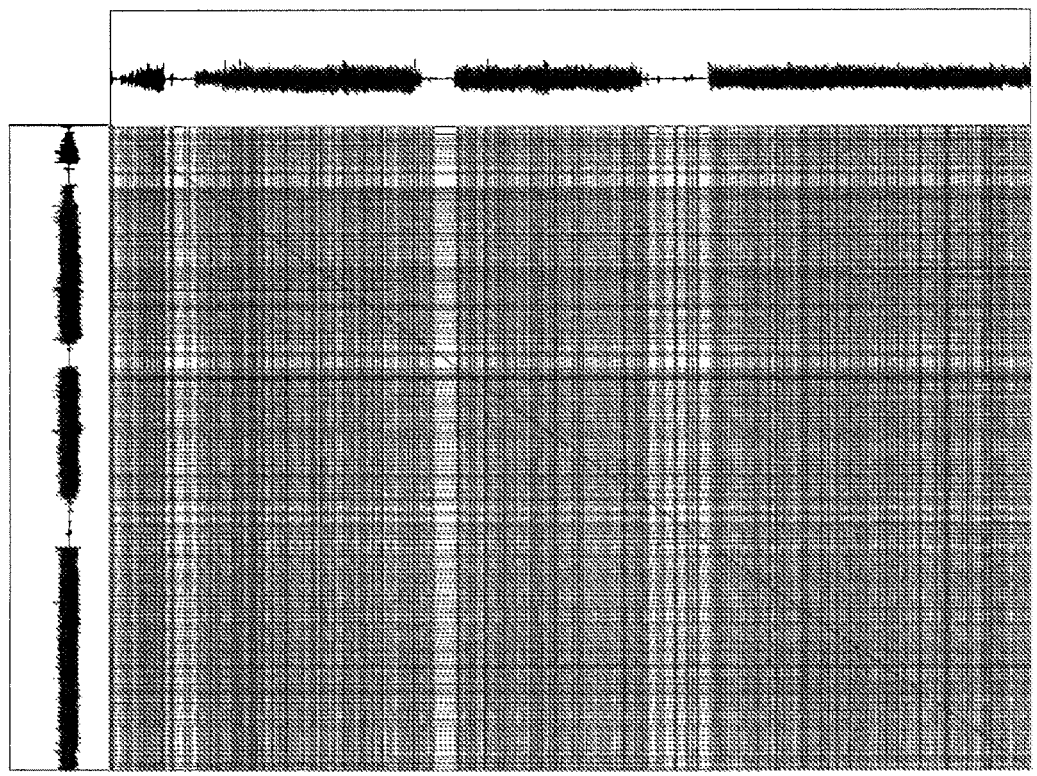
FIG. 2 is a pattern showing the method for behavior pattern analysis in a first preferred embodiment of the present invention.

FIG. 2 shows the result for behavior pattern analysis on a staff member processing document administration. The result shows that the staff member's behaviors have significant diversity, some behaviors have been happened previously while the behaviors at most time points lack correlation. The correlation coefficient of the analytic result is 0.441.

Figure 3:
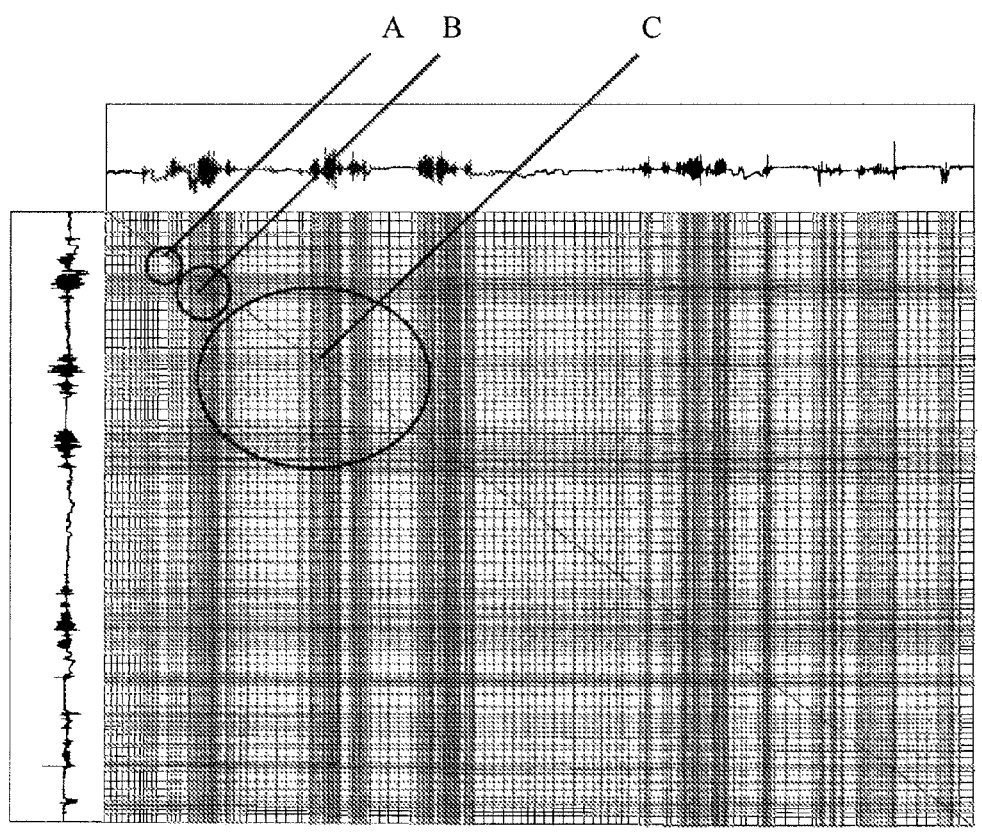
FIG. 3 is a pattern showing the method for behavior pattern analysis in a second preferred embodiment of the present invention.
Figure 4:
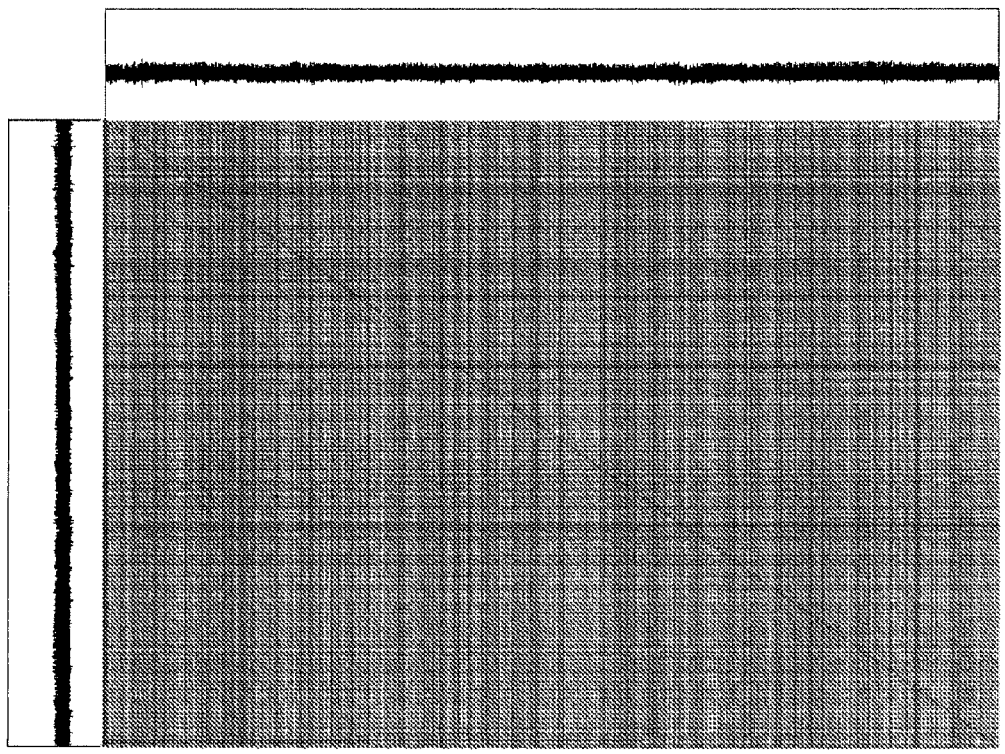
FIG. 4 is a pattern showing the method for behavior pattern analysis in a third preferred embodiment of the present invention.

FIG. 3 shows the result for behavior pattern analysis on a subject walking on the street with plural traffic lights and obstacles. The result shows that the subject's postures have significant consistency (correlation coefficient 0.712) while he changes postures frequently. For example, area A is referred to that the subject is quiescent, area B is referred to that subject has only one behavior, and area C is referred to that subject processes another behavior. FIG. 4 shows the result for behavior pattern analysis on a subject walking on the street without obstacles, wherein the subject's behaviors (FIG. 4, correlation coefficient 0.819) have better consistency than his previous behaviors (FIG. 3, correlation coefficient 0.712), and the subject's behaviors even have more significant consistency than the staff member (referring to FIG. 2).

Figure 5:
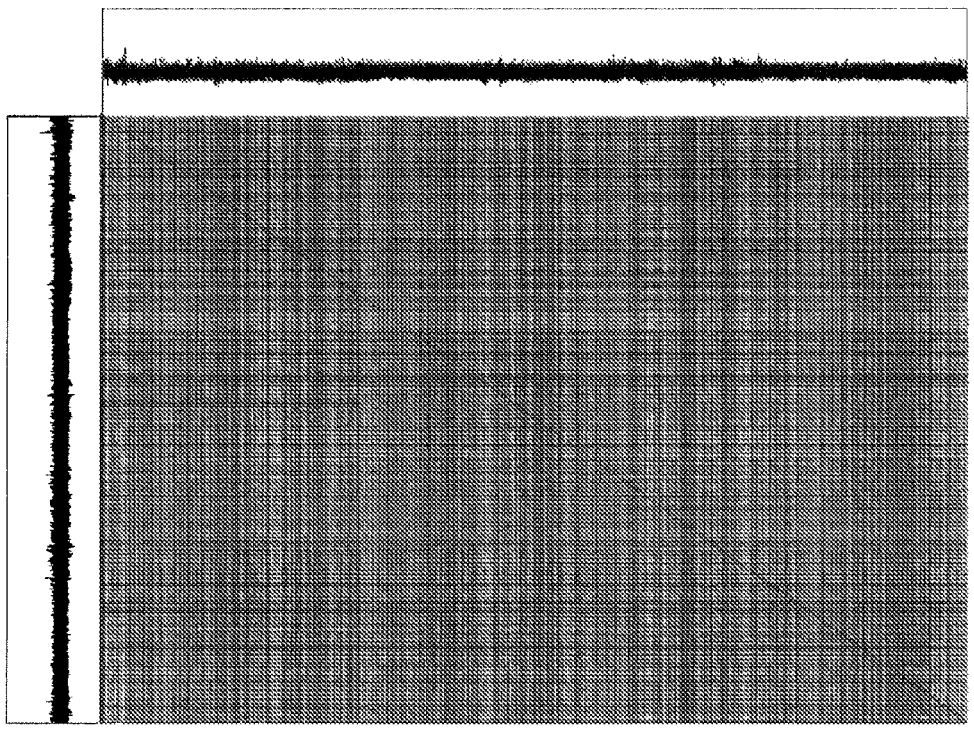
FIG. 5 is a pattern showing the method for behavior pattern analysis in a fourth preferred embodiment of the present invention.

FIG. 5 shows the analytic pattern for behavior pattern on the same subject strolling with greatest regularity, and the whole pattern represents significant consistency and relatively high correlation (correlation coefficient 0.888). It indicates that the subject strolls with the regular manner and maintains consistency during the test.

In conclusion, the behavior consistency of a subject can be efficiently evaluated by the method for behavior pattern analysis of the present invention, and the behavior abnormality, disease development or other situations of the subject can be determined accordingly.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for analyzing a behavior pattern, the method comprising:
    (a) continuously detecting behavior signals of a subject by using a device having a tri-axis accelerator;
    (b) dividing the behavior signals as n time windows based on a predetermined time length, n being a plural number;
    (c) configuring the n time windows as a matrix of an X-axis and a Y-axis;
    (d) performing a cross analysis on the n time windows at the X-axis and the n time windows at the Y-axis to obtain a plurality of preferred correlation values, converting the plurality of preferred correlation values as bright spots or dark spots, the bright spots representing a first consistency of the behavior pattern, the dark spots representing a second consistency of the behavior pattern, and the first consistency is higher than the second consistency; and
    (e) estimating a pattern according to the plurality of preferred correlation values to evaluate the behavior pattern.

2. The method according to claim 1, wherein the step (a) further comprises a step (a1) of amplifying or filtering the behavior signals.

3. The method according to claim 1, wherein the n time windows are distinguished as a zeroth time window, a first time window, ... and an (n−1)th time window, the zeroth time window at the X-axis is neighbored to the zeroth time window at the Y-axis.

4. The method according to claim 1, wherein the step (d) further is processed by a cross-correlation analysis or a cross-spectral analysis.

* * * * *